United States Patent
Ekwuribe et al.

(10) Patent No.: US 6,525,098 B1
(45) Date of Patent: Feb. 25, 2003

(54) 6-METHOXY-2-NAPHTHYLACETIC ACID PRODRUGS

(75) Inventors: Nnochiri Nkem Ekwuribe, Cary; Tatyana A. Dyakonov, Greensboro, both of NC (US)

(73) Assignee: Nobex Corporation, Durham, NC (US)

( * ) Notice: Subject to any disclaimer, the term of this patent is extended or adjusted under 35 U.S.C. 154(b) by 0 days.

(21) Appl. No.: 09/697,795

(22) Filed: Oct. 27, 2000

Related U.S. Application Data

(60) Provisional application No. 60/161,864, filed on Oct. 27, 1999.

(51) Int. Cl.[7] .................. A61K 31/19; A61K 31/12; A61K 31/05
(52) U.S. Cl. .................. 514/569; 514/682; 514/732
(58) Field of Search .................. 514/569, 682, 514/732

(56) References Cited

U.S. PATENT DOCUMENTS

| | | | |
|---|---|---|---|
| 3,883,662 A | * 5/1975 | Henzl et al. | 424/343 |
| 3,904,682 A | 9/1975 | Fried et al. | 260/520 |
| 3,978,116 A | 8/1976 | Fried et al. | 260/500.5 |
| 4,009,197 A | 2/1977 | Fried et al. | 260/473 F |
| 4,061,779 A | 12/1977 | Lake et al. | 424/331 |
| 4,246,164 A | 1/1981 | Felder et al. | 260/501.17 |
| 4,246,193 A | 1/1981 | Holton | 260/501.17 |
| 4,268,442 A | 5/1981 | Kondo et al. | 260/326.2 |
| 4,270,004 A | 5/1981 | Rose et al. | 568/314 |
| 4,327,022 A | 4/1982 | Bailey | 260/239 B |
| 4,328,356 A | 5/1982 | Giordano et al. | 560/56 |
| 4,382,959 A | * 5/1983 | Goudie | 424/331 |
| 4,420,639 A | 12/1983 | Lake et al. | 568/328 |
| 4,423,244 A | 12/1983 | Cannata et al. | 562/466 |
| 4,501,913 A | 2/1985 | Giordano et al. | 560/100 |
| 4,515,811 A | 5/1985 | Holton | 514/554 |
| 4,542,237 A | 9/1985 | Schloemer | 562/466 |
| 4,546,201 A | 10/1985 | Piccolo et al. | 562/401 |
| 4,550,191 A | 10/1985 | Castaldi et al. | 560/56 |
| 4,608,441 A | 8/1986 | Citterio et al. | 562/466 |
| 4,611,088 A | 9/1986 | Ohara et al. | 562/466 |
| 4,654,438 A | 3/1987 | Schloemer | 562/496 |
| 4,661,524 A | 4/1987 | Thomson et al. | 514/682 |
| 4,661,525 A | 4/1987 | Grazioso et al. | 518/714 |
| 4,670,586 A | 6/1987 | Yabe et al. | 562/466 |
| 4,670,603 A | 6/1987 | Piccolo et al. | 568/319 |
| 4,709,089 A | 11/1987 | Shimizu et al. | 562/494 |
| 4,723,033 A | 2/1988 | Erickson | 560/56 |
| 4,727,102 A | 2/1988 | Cannata et al. | 260/501.15 |
| 4,814,494 A | 3/1989 | Shimizu et al. | 562/419 |
| 4,851,426 A | 7/1989 | Ladkami et al. | 514/420 |
| 4,865,770 A | 9/1989 | Piselli | 562/402 |
| 4,922,009 A | 5/1990 | Villa et al. | 562/466 |
| 4,937,379 A | 6/1990 | Giordano et al. | 562/493 |
| 4,970,336 A | 11/1990 | Yoshioka et al. | 562/460 |
| 5,004,832 A | 4/1991 | Castaldi et al. | 562/490 |
| 5,068,458 A | 11/1991 | Dales et al. | 568/634 |
| 5,132,466 A | 7/1992 | Dales et al. | 568/631 |
| 5,145,993 A | 9/1992 | Kim et al. | 562/466 |
| 5,179,208 A | 1/1993 | Kim et al. | 548/230 |
| 5,200,555 A | 4/1993 | Kessels | 562/401 |
| 5,202,495 A | 4/1993 | Callander | 568/315 |
| 5,223,640 A | 6/1993 | Tafesh et al. | 562/466 |
| 5,225,603 A | 7/1993 | Aslam et al. | 568/315 |
| 5,248,815 A | 9/1993 | Paradies | 562/52 |
| 5,278,333 A | 1/1994 | Loosen et al. | 562/52 |
| 5,306,833 A | 4/1994 | Vallejos et al. | 549/79 |
| 5,426,243 A | 6/1995 | Lecouve | 568/737 |
| 5,539,000 A | 7/1996 | Leonard | 514/682 |
| 5,600,009 A | 2/1997 | Fritch et al. | 568/318 |
| 5,621,000 A | 4/1997 | Arena et al. | 514/411 |
| 5,695,774 A | 12/1997 | Clark | 424/464 |
| 5,700,947 A | 12/1997 | Soldato | 548/491 |
| 5,703,073 A | 12/1997 | Garvey et al. | 514/226.5 |
| 5,741,938 A | 4/1998 | Belmont | 568/322 |
| 5,750,764 A | 5/1998 | Marais et al. | 560/56 |
| 5,750,793 A | 5/1998 | Cannata et al. | 568/315 |
| 5,756,851 A | 5/1998 | Becnel et al. | 568/328 |
| 5,777,170 A | 7/1998 | Bellani | 568/322 |
| 5,780,495 A | 7/1998 | Del Soldato | 514/413 |
| 5,792,886 A | 8/1998 | Sabahi et al. | 568/634 |
| 5,847,225 A | 12/1998 | Ramachandran et al. | 568/328 |
| 5,861,538 A | 1/1999 | Theriot | 568/313 |
| 5,874,614 A | 2/1999 | Phan et al. | 562/467 |
| 5,907,069 A | 5/1999 | Becnel et al. | 568/737 |
| 5,955,635 A | 9/1999 | Cabri et al. | 568/314 |
| 6,057,347 A | 5/2000 | Garvey et al. | 514/364 |

FOREIGN PATENT DOCUMENTS

| | | | | |
|---|---|---|---|---|
| WO | WO 9404484 | 3/1994 | ......... | C07C/229/42 |
| WO | WO 9412463 | 6/1994 | ......... | C07C/203/04 |
| WO | PCT/EP95/01233 | 4/1995 | ......... | C07C/203/04 |
| WO | WO 9731654 | 9/1997 | .......... | A16K/45/06 |

OTHER PUBLICATIONS

"4–(6–Methoxy–2–naphtyl)butan–2–one and related analogs, a novel structural class of antiinflammatory compounds", Goudie et al, J. Med. Chem, 1978, 21(12), 1260–4; Abstract.*

(List continued on next page.)

Primary Examiner—Marianne C. Seidel
Assistant Examiner—Brian-Yong Kwon
(74) Attorney, Agent, or Firm—Myers Bigel Sibley & Sajovec, P.A.

(57) ABSTRACT

The present invention provides therapeutically effective amounts of 6MNA prodrugs. The pharmaceutical composition comprises

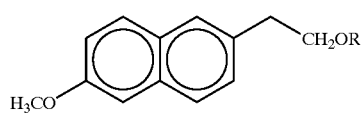

wherein R is H or COR', wherein R' is selected from the group consisting of $C_1$ to $C_6$ alkyl, $(CH_2)_m O(CH_2)_n$, $(CH_2)_m (OC_2H_4)_p O(CH_2)_n$, $(CH_2)_m(OC_2H_4)_p$, $(OCH_2H_4)_p ONO_2$ and $(OCH_2H_4)_p O(CH_2)_n$ wherein m is an integer from 2 to 4, and n and p are integers from 1 to 4. Alternatively, R is a therapeutic moiety.

2 Claims, 1 Drawing Sheet

OTHER PUBLICATIONS

Wadhwa, et al., "Glycolamide esters of 6–methoxy–2–napthtylacetic acid as potential pro–drugs–Synthetic and spectral studies", Indian Journal of Chemistry, vol. 34B, May 19995 (pp. 408–415).

Mangan, et al., "Preclinical Overview of Nabumetone", The American Journal of Medicine, vol. 83 (suppl. 4B), Oct. 1987 (pp. 6–10).

Jeremy, et al., "Effects of Prodrug Nabumetone, and its Active Metabolite, 6–MNA, on Human and Rat Gastric Mucosal Prostanoids and Platelet Function", Drugs 40 (Suppl. 5), 1990 (pp. 53–56).

Benoni, et al., "Plasma Concentrations and Pharmacokinetic Parameters of Nitrofenac Using a Simple and Sensitive HPLC Method", Journal of Pharmaceutic Sciences, vol. 84, No. 1, Jan. 1995 (pp. 93–95).

Brett, et al., "Nabutemone, Evidence for the Lack of Enterohepatic Circulation of the Active Metabolite 6–MNA in Humans", Drugs 40 (Suppl. 5), 1990 (pp. 67–70).

Hellberg et al., "Novel Esters and Amides of Nonsteroidal Antiinflammatory Carboxylic Acids as Antioxidants and Antiproliferative Agents", *J. Med. Chem.,*42(2): 267–276 (1999).

Martha Hyneck, "An Overview of the Clinical Pharmacokinetics of Nabumetone,"*The Journal of Rheumatology*, 19(36): 20–24 (1992).

International Search Report corresponding to PCT/US 00/29757: date of mailing: Sep. 14, 2001.

Paris et al., "Glycerides as Prodrugs. 4. Synthesis and Antiinflammatory Activity of 1,3–dialkanoyl–2–arlaklanoylglycerides", *Eur. J. Med. Chem.,*17(2): 193–195 (1982).

Stephen L. Dahl, "Nabumetone: A 'Nonacidic'Nonsteroidal Antiinflammatory Drug", *The Annals of Pharmacology*, 27: 456–463 (Apr.1993).

Soma et al., "Disposition and Excretion of 6–Methoxy–2–Naphthylacetic Acid, the Active Metabolite of Nabumetone in Horses", *AJVR*, 57(4): 517–521 (Apr. 1996).

International Search Report corresponding to PCT/US 00/41692; Date of Mailing: Oct. 11, 2001.

* cited by examiner

6-METHOXY-2-NAPHTHYLACETIC ACID PRODRUGS

RELATED APPLICATION

This application claims priority from United States Provisional Application 60/161,864, filed Oct. 27, 1999, the disclosure of which is incorporated by reference herein in its entirety.

FIELD AND BACKGROUND OF THE INVENTION

The present invention relates to pharmaceutical compositions useful for treatment of inflammation in humans utilizing compounds that are prodrugs of 6-methoxy-2-naphthylacetic acid (hereinafter "6MNA").

Various naphthalene derivatives are known to be useful for the treatment of inflammation and for various rheumatic and arthritic conditions. For example, Naproxen having the formula (I):

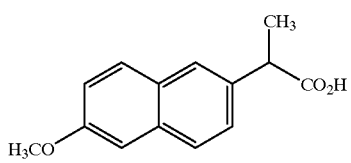

as described in U.S. Pat. No. 4,009,197 to Fried et al. Compound (I) can, however, cause severe irritation of the gastronintestinal tract at dosages only slightly greater than the excess of the therapeutic dose.

Another naphthalene derivative is nabumetone having the formula (II):

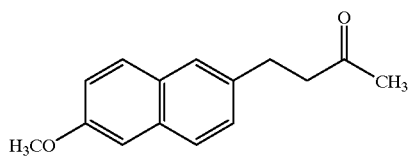

as described in U.S. Pat. Nos. 4,061,779 and 4,420,639 to Lake et al. Nabumetone works by inhibiting cyclooxygenase, an enzyme responsible for making prostaglandins which are mediators of inflammation. Nabumetone is a prodrug which undergoes hepatic biotransformation to the active component, 6-methoxy-2-naphthylacetic acid, Formula (III):

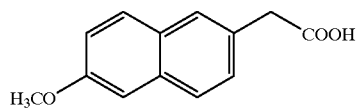

(See Haddock, R. E. et al; Metabolism of Nabumetone (BRL 14777 by various species including man," Xenobiotica; 14(4): 327–337 (1984)). Nabumetone is commercially available as Relafen® from Smithkline Beecham, Inc. However, only about 35 percent of orally administered nabumetone is transferred in vivo into 6MNA.

It is therefore an object of the present invention to provide 6MNA prodrugs which are more readily transformed into 6MNA than nabumetone. It is believed that improvement in the body's ability to hydrolyze and solubilize the prodrug can contribute to this transformation. Thus, it is another object to improve the hydrolysis and solubility of the prodrug to provide better transformation to 6MNA.

Another concern with 6MNA and its related prodrugs is that the presence of the carboxylic acid moiety can cause stomach irritation and/or ulceration. Thus, it is another object of the present invention that provides prodrugs of 6MNA having a reduced propensity to cause stomach irritation.

SUMMARY OF THE INVENTION

As discussed above, the present invention provides therapeutically effective amounts of 6MNA prodrugs. It is believed that the 6MNA prodrug of the invention has improved hydrolysis and solubility. It is believed that the prodrugs of the invention are useful for the treatment of inflammation in humans, and can provide analgesic and antipyretic properties.

The pharmaceutical composition comprises

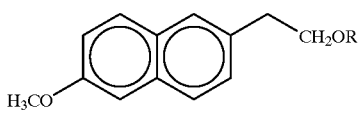

wherein R is selected from the group consisting of H and COR', wherein R' is selected from the group consisting of $C_1$ to $C_6$ alkyl, $(CH_2)_m$ $O(CH_2)_n$, $(CH_2)_m(OC_2H_4)_p$ $O(CH_2)_n$, $(CH_2)_m(OC_2H_4)_p$, $(OCH_2H_4)_p$ $ONO_2$ and $(OCH_2H_4)_p$ $O(CH_2)_n$ wherein m is an integer from 2 to 4, and n and p are integers from 1 to 4. Alternatively, R is a therapeutic moiety.

The foregoing and other aspects of the present invention are explained in detail in the detailed description and example set forth below.

DETAILED DESCRIPTION OF THE INVENTION

Figure 1:
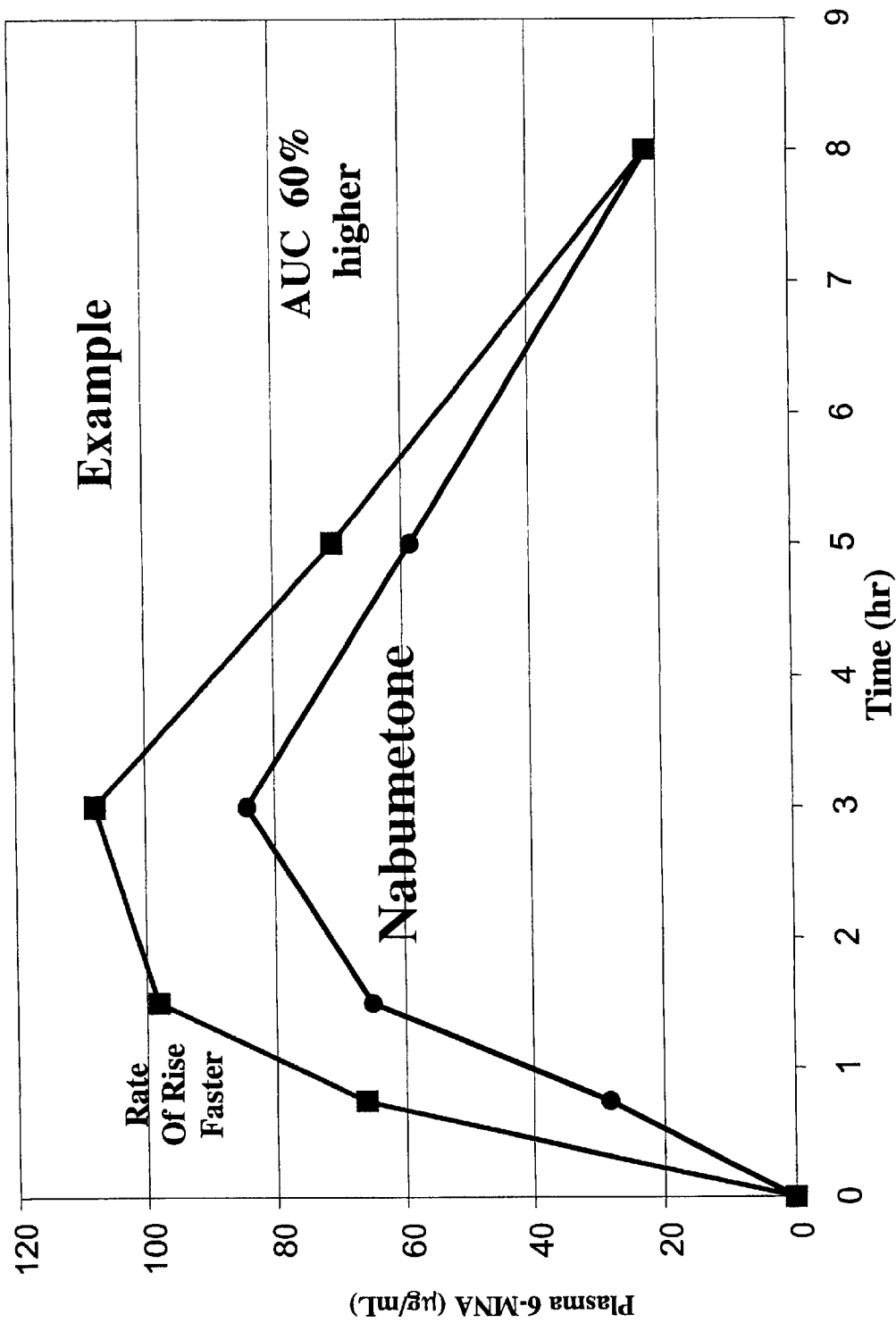
FIG. 1 is a graph of in plasma levels of Example 1 compared to Nabumetone.

The present invention will now be described more fully hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

A "therapeutically effective amount" is an amount necessary to prevent, delay or reduce the severity of inflammation and also includes an amount necessary to enhance normal physiological functioning.

As used herein, a "pharmaceutically acceptable" component (such as a salt, carrier, excipient or diluent) of a formulation according to the present invention is a component which (1) is compatible with the other ingredients of the formulation in that it can be combined with the 6MNA prodrugs of the present invention without eliminating the biological activity of the 6MNA prodrugs; and (2) is suitable for use with an animal (e.g., a human) without undue adverse side effects, such as toxicity, irritation, and allergic response. Side effects are "undue" when their risk outweighs the benefit provided by the pharmaceutical composition.

In one embodiment, the pharmaceutical composition is

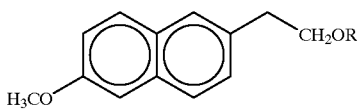

wherein R is selected from the group consisting of is H and COR' wherein R' is selected from the group consisting of $C_1$ to $C_6$ alkyl, $(CH_2)_m\ O(CH_2)_n$, $(CH_2)_m(OC_2H_4)_p\ O(CH_2)_n$, $(CH_2)_m(OC_2H_4)_p$, $(OCH_2H_4)_p\ ONO_2$ and $(OCH_2H_4)_p\ O(CH_2)_n$ wherein m is an integer from 2 to 4, and n and p are integers from 1 to 4.

In a preferred embodiment R is H, and such composition converts directly to the active drug 6MNA.

In another embodiment, R is a therapeutic moiety such as

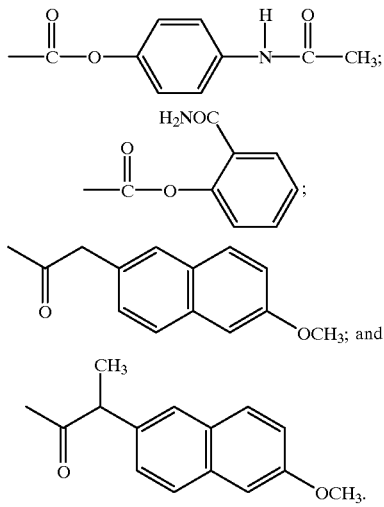

Such prodrug composition can advantageously be used to treat inflammation, and also provide analgesic and antipyretic properties. 6MNA prodrugs of the present invention may optionally be administered in conjunction with other compounds useful in the treatment of inflammation or useful in treatment of other indications associated with inflammation such as pain. The other compounds may optionally be administered concurrently. As used herein, the word "concurrently" means sufficiently close in time to produce a combined effect (that is, concurrently may be simultaneously, or it may be two or more events occurring within a short time period before or after each other).

As used herein, the administration of two or more compounds "in combination" means that the two compounds are administered closely enough in time that the presence of one alters the biological effects of the other. The two compounds may be administered simultaneously (i.e., concurrently) or sequentially. Simultaneous administration may be carried out by mixing the compounds prior to administration, or by administering the compounds at the same point in time but at different anatomic sites or using different routes of administration.

The phrases "concurrent administration," "administration in combination," "simultaneous administration" or "administered simultaneously" as used herein, interchangeably mean that the compounds are administered at the same point in time or immediately following one another. In the latter case, the two compounds are administered at times sufficiently close that the results observed are indistinguishable from those achieved when the compounds are administered at the same point in time.

The present invention is primarily concerned with the treatment of human subjects, but the invention may also be carried out on animal subjects, particularly mammalian subjects such as mice, rats, dogs, cats, livestock and horses for veterinary purposes, and for drug screening and drug development purposes.

The 6MNA prodrugs disclosed herein can, as noted above, be prepared in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, malic acid, ascorbic acid, benzoic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

The 6MNA prodrugs described above may be formulated for administration in a pharmaceutical carrier in accordance with known techniques. See, e.g., Remington, *The Science And Practice of Pharmacy* ($9^{th}$ Ed. 1995). In the manufacture of a pharmaceutical formulation according to the invention, the prodrug (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the 6MNA prodrug. One or more 6MNA prodrugs may be incorporated in the formulations of the invention, which may be prepared by any of the well known techniques of pharmacy consisting essentially of admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular 6MNA prodrug which is being used.

Formulations suitable for oral administration may be presented in discrete units, such as capsules, cachets, lozenges, or tables, each containing a predetermined amount of the 6MNA prodrug; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the 6MNA prodrug and a suitable carrier (which may contain one or more accessory ingredients as noted above). In general, the formulations of the invention are prepared by uniformly and intimately admixing the 6MNA prodrug with a liquid or finely divided solid carrier, or both, and then, if necessary, shaping the resulting mixture. For example, a tablet may be prepared by compressing or molding a powder or granules containing the 6MNA prodrug, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the 6MNA prodrug in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the 6MNA prodrug, which preparations are preferably isotonic with the blood of the intended recipient. These preparations may contain antioxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising a compound of Formula (I), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the 6MNA prodrug with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the 6MNA prodrug. Suitable formulations comprise citrate or bis\tris buffer (pH6) or ethanol/water and contain from 0.1 to 0.2M active ingredient.

The therapeutically effective dosage of any 6MNA prodrug, the use of which is in the scope of present invention, will vary somewhat from compound to compound, and patient to patient, and will depend upon factors such as the age and condition of the patient and the route of delivery. Such dosages can be determined in accordance with routine pharmacological procedures known to those skilled in the art.

The therapeutically effective dosage of any specific compound, the use of which is in the scope of present invention, will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the 6MNA prodrug, including the cases where a salt is employed. Toxicity concerns at the higher level may restrict intravenous dosages to a lower level such as up to about 10 mg/kg, with all weights being calculated based upon the weight of the active base, including the cases where a salt is employed. A dosage from about 10 mg/kg to about 50 mg/kg may be employed for oral administration. Typically, a dosage from about 0.5 mg/kg to 5 mg/kg may be employed for intramuscular injection. The duration of the treatment is usually once per day for a period of two to three weeks or until the condition is essentially controlled. Lower doses given less frequently can be used prophylactically to prevent or reduce the incidence of recurrence of the infection.

EXAMPLE

Example 1

Synthesis of 2-(6-Methoxy-naphthalen-2-yl)-ethanol

6-MNA (1g, 0.0046 mol) was suspended in anhydrous THF and was cooled with ice bath suspension BH3(1 M solution in THF, 5 ml)was added. The reaction mixture was stirred for 3 hours then Dl water and sodium carbonate added. THF was removed and aqueous phase extracted with ethyl acetate then washed with water, dried over Na2SO4, filtered concentrated and dried via vacuum.

Yield 93%. Melting point 110–113° C. product was analyzed by elemental analysis, IR, MS, NMR. MS 202.10 IR (cm$^{-1}$) Elemental analysis: C 56.18; H 4.28; N 4.03 NMR 1H Analysis of blood samples in rats after oral delivery showed a conversion of the compound of Example 1 to the active drug 6MNA. Example 1 had a rat paw edema, % inhibition of 67.5 as compared to 60.0 for Nabumetone. FIG. 1 shows higher plasma levels, with more rapid onset, are achieved with Example 1 as compared to Nabumetone.

Analysis of blood samples in rats after oral delivery showed a conversion of the compound of Example 1 to the active drug 6MNA.

The foregoing is illustrative of the present invention and is not to be construed as limiting thereof. The invention is defined by the following claims, with equivalents of the claims to be included therein.

That which is claimed is:

1. A pharmaceutical composition useful for treatment of inflammation to humans comprising a therapeutically effective amount of a compound of the formula:

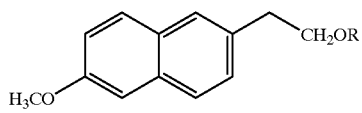

wherein R is selected from the group consisting of:

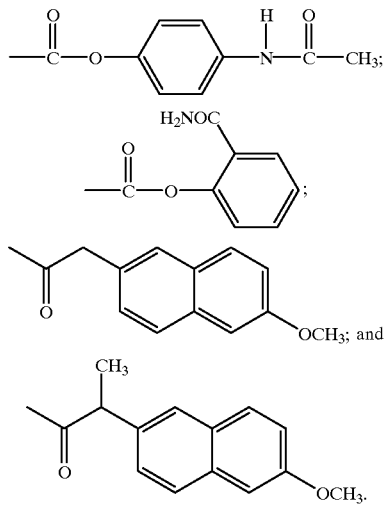

2. A method of treating inflammation comprising administering a therapeutically effective amount of a compound of the formula:

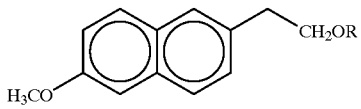

wherein R is selected from the group consisting of:

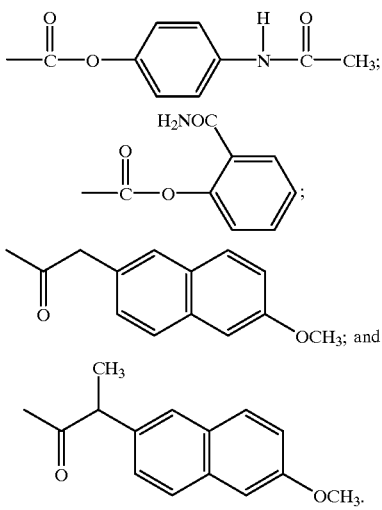

* * * * *

UNITED STATES PATENT AND TRADEMARK OFFICE
CERTIFICATE OF CORRECTION

PATENT NO. : 6,525,098 B1  Page 1 of 1
DATED : February 23, 2003
INVENTOR(S) : Ekwuribe et al.

It is certified that error appears in the above-identified patent and that said Letters Patent is hereby corrected as shown below:

Title page,
Item [56], References Cited, U.S. PATENT DOCUMENTS, the "4,727,102" patent reference should be replaced with the following:
-- 4,724,102 A  2/1988  Cannata et al. ….. 260/501.15 --
The following patent reference should be included:
-- 5,840,996  11/24/1998  Sabahi  ….. 568/634 --
The following patent references should be included:
FOREIGN PATENT DOCUMENTS
-- EP    0974584    01/26/2000    C07D/213/06 --
OTHER PUBLICATIONS, the "Paris et al." reference should read as follows:
  -- Paris et al., "Glycerides as Prodrugs. 4. Synthesis and Antiinflammatory Activity of 1,3-dialkanoyl-2-arylak-lanoylglycerides", *Eur. J. Med. Chem*, 17(2): 193-195 (1982).
The following references should be included:
-- Harris et al., "Anti-Inflammatory (AI) Efficacy and Acute Gastrointestinal Irritancy (GI) Profile for a Series of Novel 6-Methoxy-2-Naphthylacetic Acid (6-MNA)-Prof-Drugs, "*Inflammation Research*, 49(2):S97 (2000).
  Summers et al., "Hydroxamic Acid Inhibitors of 5-Lipoxygenase: Quantitative Structure-Activity Relationships," *J. Med. Chem.*, 33(3): 992-998-(1990).
  Nielsen, N. & Bundgaard, H., "Glycolamide Esters as Biolabile Prodrugs of Carboxylic Acid Agents: Synthesis, Stability, Bioconversion, and Physicochemical Properties," *Journal of Pharmaceutical Sciences*, 77(4): 285-298 (1988).
  Schwenker, G., & Stiefvater, K., "Hydrolysegeschwindigkeit von 5-Acyloxy-1, 3-dioxolan-4-onen," *Archiv der Pharmazie*, 324(7): 439-444 (1991).
  Wadwha, L. & Sharma, P., "Glycolamide Esters of 6-Methoxy-2-Naphthylacetic Acid as Potential Prodrugs – Physicochemical Properties, Chemical Stability and Enzymatic Hydrolysis," *International Journal of Pharmaceutics*, 118(1): 31-39 (1995).

Signed and Sealed this

Twenty-second Day of July, 2003

JAMES E. ROGAN
*Director of the United States Patent and Trademark Office*